United States Patent
Miller et al.

(10) Patent No.: US 6,825,770 B2
(45) Date of Patent: Nov. 30, 2004

(54) LOW PRESSURE ALARM ASSEMBLY

(75) Inventors: Kenneth G. Miller, Costa Mesa, CA (US); Myron Rich, Exeter, CA (US)

(73) Assignee: The Source Enterprises Inc., Santa Ana, CA (US)

( * ) Notice: Subject to any disclaimer, the term of this patent is extended or adjusted under 35 U.S.C. 154(b) by 44 days.

(21) Appl. No.: 10/137,752

(22) Filed: May 2, 2002

(65) Prior Publication Data

US 2003/0206110 A1 Nov. 6, 2003

(51) Int. Cl.[7] .............................................. G08B 21/00
(52) U.S. Cl. ...................................... 340/626; 340/688
(58) Field of Search ................................. 340/688, 626, 340/686, 438, 614; 73/1.37, 732, 733

(56) References Cited

U.S. PATENT DOCUMENTS

| | | | | |
|---|---|---|---|---|
| 3,593,582 A | * | 7/1971 | Birkmeyer | 73/733 |
| 4,536,756 A | * | 8/1985 | DePasquale et al. | 340/626 |
| 4,613,851 A | * | 9/1986 | Hines | 340/688 |
| 4,906,977 A | * | 3/1990 | Huey-Jeng | 340/626 |
| 5,357,242 A | * | 10/1994 | Morgano et al. | 340/626 |
| 5,700,956 A | * | 12/1997 | Huang | 73/735 |
| 6,326,896 B1 | * | 12/2001 | McDermott et al. | 340/626 |

* cited by examiner

*Primary Examiner*—Anh V. La
(74) *Attorney, Agent, or Firm*—Olson & Hierl, Ltd.

(57) ABSTRACT

A low pressure alarm assembly where a switch for activating a low pressure alarm is operably associated with a link assembly which is operably actuable in response to the movement of a pressure responsive element. In one embodiment, the link assembly incorporates a pointer which is adapted to sweep across the plate of a pressure gauge into contact with the switch to close the switch and activate the low pressure alarm.

7 Claims, 4 Drawing Sheets

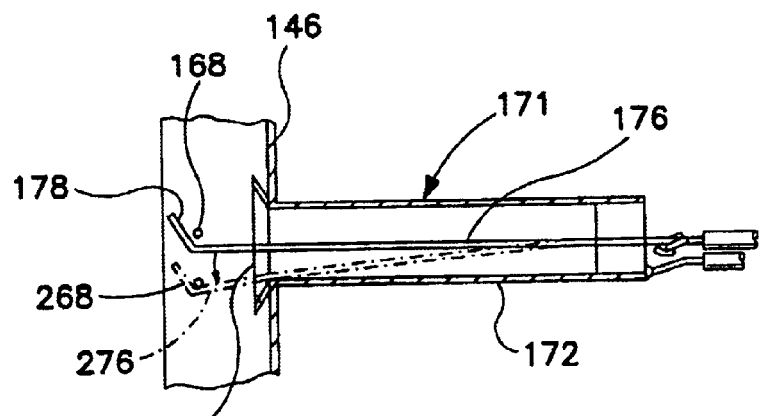
FIG. 7
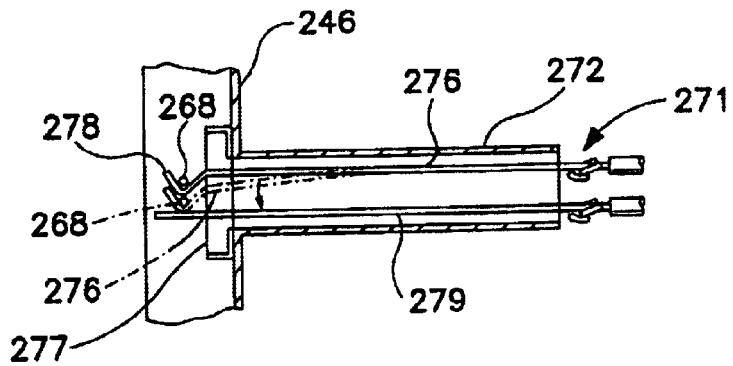
FIG. 8
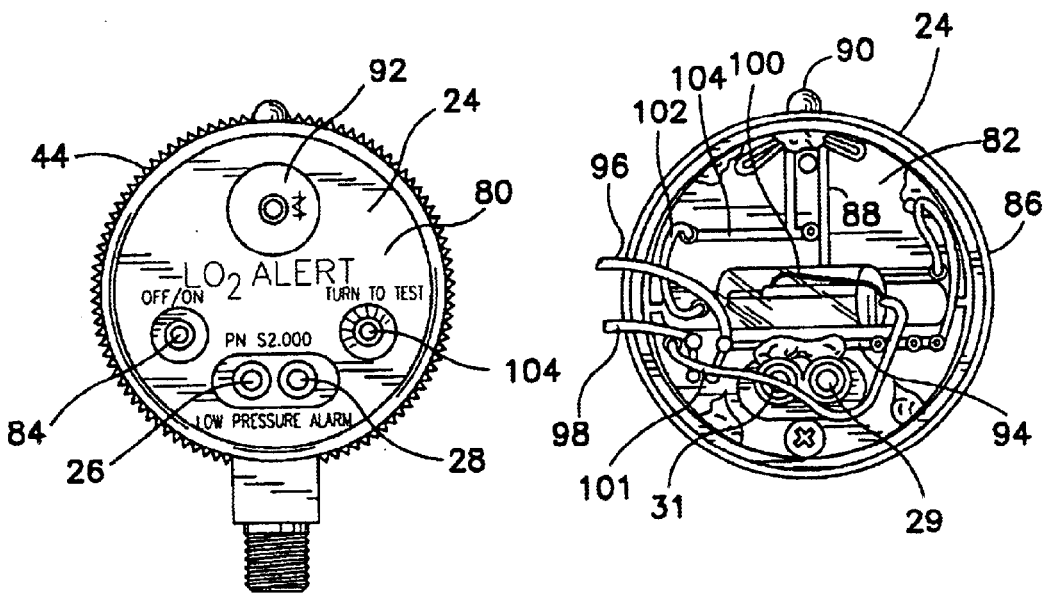
FIG. 9
FIG. 10

LOW PRESSURE ALARM ASSEMBLY

FIELD OF INVENTION

The invention relates to a low pressure alarm assembly and, more particularly, to a low pressure alarm assembly incorporating an electrical alarm switch which is activated through a link assembly and pressure indicator operably coupled to a pressure sensing tube.

BACKGROUND OF THE INVENTION

Oxygen tanks are used in respiratory therapy applications where central oxygen systems are not accessible or available. The oxygen supplied by these tanks is typically regulated to about 50 PSI with a standard regulator/gauge manifold. The pressure in these oxygen tanks is typically about 3000 PSI when full but naturally drops during use as the oxygen is consumed from the tank. One of the problems associated with the use of a simple regulator/gauge manifold is the obvious potential patient hazard that results when the tank runs dry without notice. This problem is particularly common in noisy hospital or clinic environments where, due to the relatively quiet delivery of the oxygen, a tank may run out of oxygen without being noticed.

One device which causes the activation of an alarm when the pressure in the tank falls below a predetermined level is disclosed in U.S. Pat. No. 3,593,582 where the alarm assembly includes two separate pressure sensing members, i.e., a bourdon type gauge or tube operably associated with a pressure indicator and a bellows type gauge associated with an electrical switch actuable to activate a low pressure alarm. A disadvantage associated with this device however is that it requires two separate pressure sensing members, i.e., one which is used in connection with an indicator to measure the pressure and another which is operably associated with a switch to activate the alarm.

The present invention provides an improved low pressure alarm assembly including only one pressure sensing member and where the electrical switch adapted to activate the low pressure alarm is directly operably associated with a link assembly and the pressure indicator associated with the pressure sensing member.

The present invention also provides an improved low pressure alarm incorporating an electrical circuit which allows a visual and/or audible alarm to be tested either prior to or during use of the assembly. Further, an on-off switch allows the alarm to be disabled following activation.

SUMMARY OF THE INVENTION

A low pressure alarm assembly of the present invention includes a pressure gauge having a housing, a pressure-responsive element in the housing and adapted for communication with a fluid pressure source, a calibrated dial plate mounted in the housing, a pointer operably associated with the pressure-responsive element and mounted in the housing to sweep the dial plate in response to pressure change in the fluid pressure source, and an alarm assembly in the housing and including an alarm energization circuit with a normally open switch. In accordance with one embodiment of the invention, the pointer is positioned to close the normally open switch when pressure of the fluid pressure source is at a predetermined level.

In one embodiment of the present invention, the pointer is part of the alarm energization circuit. In another embodiment, the pointer is separate from the alarm energization circuit and energizes a switch such as, for example, a proximity switch mounted in the dial plate at a predetermined location.

A linkage assembly, also in the housing, operably couples the pressure-responsive element which, in one embodiment, is a pressure sensing tube to the pointer which sweeps the dial plate. In accordance with one embodiment of the invention, the alarm assembly is operably coupled to the linkage assembly and is actuable in response to the predetermined movement of the linkage assembly to activate a low pressure alarm.

In another embodiment, the alarm assembly switch has first and second contacts which extend outwardly through the plate of the housing, the pointer is separate from the alarm energization circuit, and the pointer is adapted to abut and force the second contact into abutting relationship with the first contact for closing the switch and activating the alarm in response to the movement of the pointer to a predetermined low pressure marking.

The first contact may take the form of a tube extending through the housing and defining an opening in the plate and the second contact may take the form of an elongate wire extending through the tube and terminating in an end protruding through the opening defined in the tube.

In another embodiment, the linkage assembly includes a lever arm which is operably associated with the closed end of the pressure sensing tube and moves in response to the movement of the pressure sensing tube and the alarm assembly includes a proximity switch having a contact operably associated with the lever arm and adapted to shift between open and closed switch positions in response to the movement of the lever arm.

The low pressure alarm assembly of the present invention also includes an alarm housing which houses audible and/or visual alarms which are operably associated with a battery which is operably associated with the switch.

A test switch associated with the alarm housing is operably electrically associated with the audible alarm, the visual alarm and the battery to allow the alarm to be tested both prior to and during use of the assembly.

Further, an on/off switch is associated with the alarm housing and is operably electrically connected to the audible alarm, the visual alarm, the switch and the battery to allow the alarm to be turned off following activation.

Other advantages and features of the present invention will be more readily apparent from the following detailed description of the preferred embodiments of the invention, the accompanying drawings, and the appended claims.

BRIEF DESCRIPTION OF THE DRAWINGS

In the drawings,

FIG. 7 is a simplified, enlarged, broken side elevational view of another embodiment of the alarm switch of the assembly of the present invention;

FIG. 8 is a simplified, enlarged, broken side elevational view of yet another embodiment of the alarm switch of the assembly of the present invention;

FIG. 9 is an elevational view of the back wall of the alarm circuit housing of the assembly of the present invention;

FIG. 10 is a front elevational view of the interior of the alarm circuit housing of the assembly of the present invention;

DETAILED DESCRIPTION OF THE PREFERRED EMBODIMENTS

Figure 1:
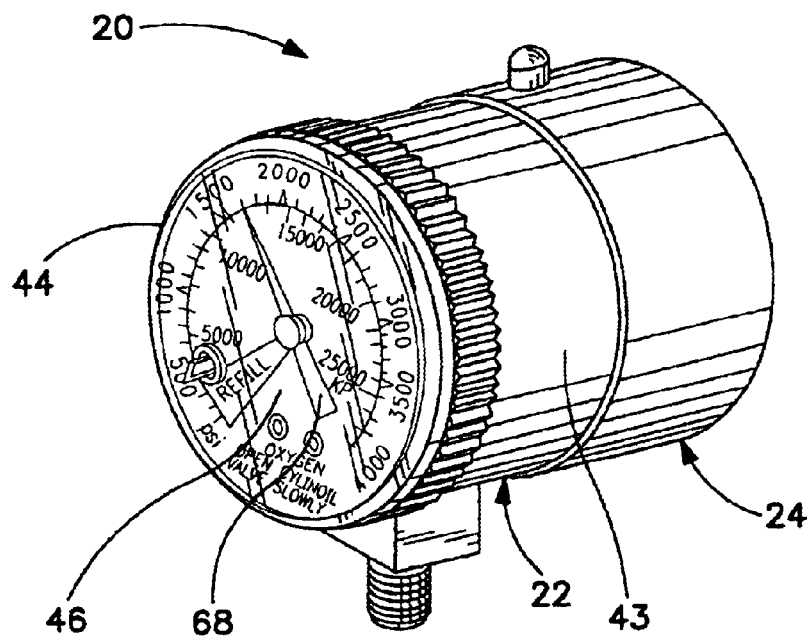
FIG. 1 is a perspective view of a low pressure alarm assembly embodying the features of the present invention.

The invention disclosed herein is, of course, susceptible of embodiment in many different forms. Shown in the drawings and described below in detail are preferred embodiments of the low pressure alarm assembly of the present invention. It is to be understood, however, that the present disclosure is an exemplification of the principles of the invention and does not limit the invention to the illustrated embodiments.

For ease of description, the low pressure alarm assembly of the present invention will be described in a normal (upright) operating position and terms such as upper, lower, horizontal, etc., will be used with reference to this position. It will be understood, however, that the low pressure alarm assembly of the present invention may be manufactured, stored, transported, used, and sold in an orientation other than the position described.

Moreover, the FIGURES and the description omit details of the structure of certain of the elements of the assembly such as, for example, the bourdon tube, the associated pressure sensing and measuring linkages, and the electrical switches, all of which are known in the art and will be recognized by those skilled in the art as such. The detailed descriptions of such elements are not necessary to an understanding of the invention. Accordingly, such elements are herein represented only to the degree necessary to aid an understanding of the features of the present invention.

Figure 2:
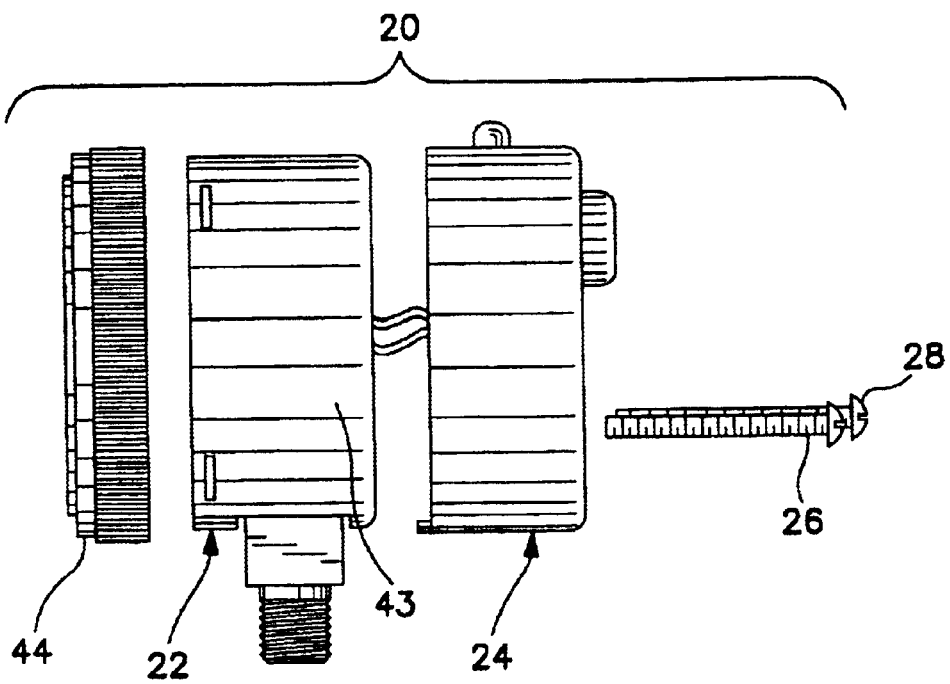
FIG. 2 is an exploded side elevational view of the assembly of FIG. 1.
Figure 3:
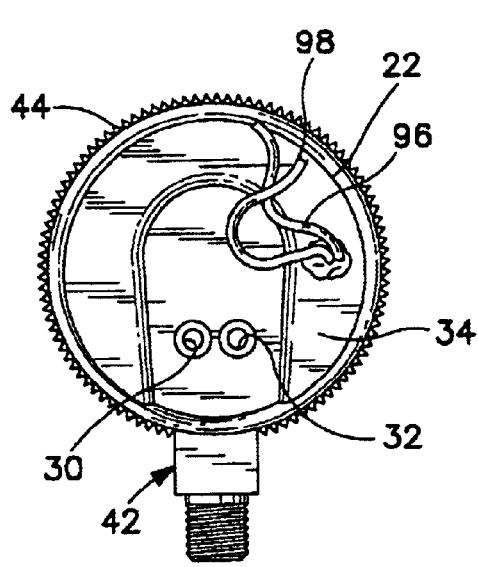
FIG. 3 is an elevational view of the back of the housing of the assembly of FIG. 1 which houses the pressure sensing and measuring components.
Figure 4:
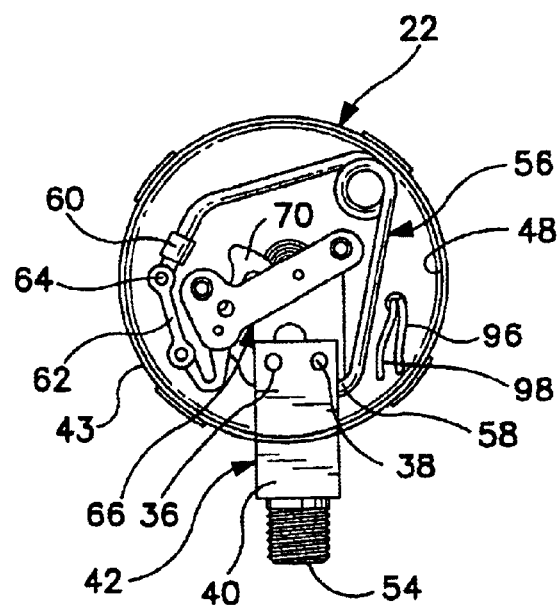
FIG. 4 is a rear elevational view of the back of the housing of FIG. 3, with the back wall thereof broken away.

A low pressure alarm assembly 20 constructed in accordance with the present invention is illustrated in FIGS. 1 and 2. As shown therein, the assembly 20 is comprised of two separate, generally cylindrically shaped, hollow housings 22 and 24 which are joined and secured together by screws 26 and 28 which extend successively through respective threaded apertures 29 and 31 defined in the housing 24 (FIG. 10), threaded apertures 30 and 32 defined in the back wall 34 of the housing 22 (FIG. 3) and then through threaded apertures 36 and 38 defined in the block 40 forming part of an inlet fitting 42 contained in the interior of the housing 22 (FIG. 4). The housing 22 houses the pressure gauge 23 and alarm switch components of the assembly of the present invention while the housing 24 houses the alarm testing and circuit components of the assembly of the present invention.

The housing 22 includes a circumferential wall 43, which at the front end thereof, supports a transparent window member 44 through which may be seen a plate or face 46 which, in the embodiment shown, has imprinted thereon a plurality of predetermined markings including calibrated pressure markings ranging from 0 to 4000 PSI. As shown in FIG. 3, the housing 22 is closed at the rear by the wall 34. The housing 22 defines an interior 48 (FIG. 4) which houses the inlet fitting 42 including the block 40 which has a proximal portion mounted to the back of the plate 46 and a distal portion extending through an opening (not shown) defined in the bottom of the housing wall 43. The block 40 terminates in a threaded inlet nozzle 54 adapted to be connected to a source of fluid pressure (not shown) such as a pressurized oxygen tank.

As shown in FIG. 4, the block 40 is adapted to support, and is in fluid communication with, a pressure responsive member which, in the embodiment shown, is a conventional bourdon gauge or hollow tube 56 having one end 58 connected to, and in fluid flow communication with, the interior of the valve block 40. The bourdon tube 56 also includes a top elongate tube segment 59 terminating in a free end 60 which is capped and adapted to move or shift up or down, as is known in the art, in response to an increase or decrease in fluid pressure of the medium in the block 40.

As is also known in the art, the associated linkage which allows the pressure to be measured and indicated includes lever arm 62 which has an end 64 to which the free end 60 of tube 56 is secured. The lever arm 62 is in turn mounted for pivotal movement relative to a lever pivotal member 66 secured to the back of the plate 46. The member 66, in turn, acts as a pivot for an indicator or pointer 68 (FIGS. 1 and 5) which is adapted to sweep across the front of the plate 46 to indicate the amount of pressure acting within the bourdon tube 56. A pendulum member 70 associated with the pivot member 66 pivotally interconnects the lever arm 64 and the indicator 68.

Figure 5:
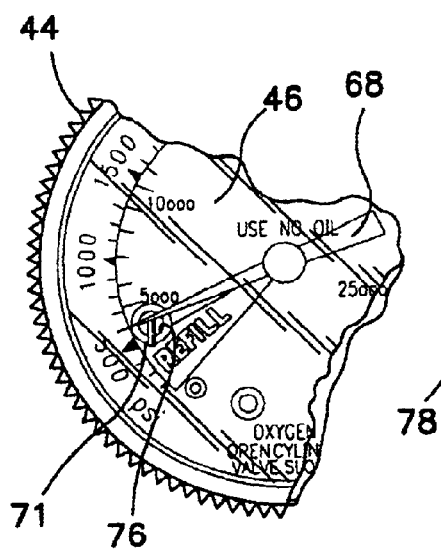
FIG. 5 is an exploded, broken elevational view of the front face of the housing of FIG. 3.
Figure 6:
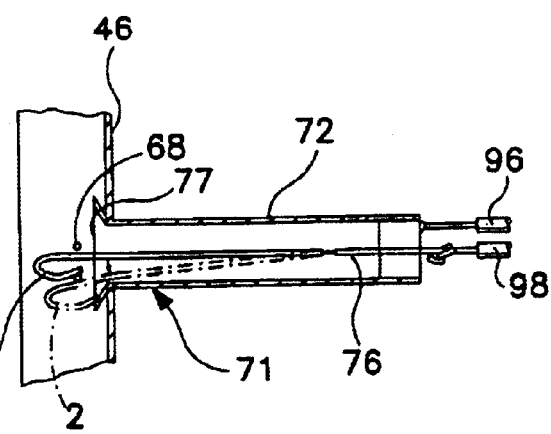
FIG. 6 is a simplified, enlarged, broken side elevational view of the alarm switch of the assembly of the present invention.

Further, and as shown in FIGS. 5 and 6, a normally open electrical alarm actuating switch or gauge 71 is operably associated with the indicator 68. In the embodiment of FIGS. 5 and 6, the switch 71 comprises an electrically conductive hollow tube 72 defining a first electrical contact extending through the housing 22 and including an open front end defining a peripheral circumferentially extending surface or opening 77 protruding through the plate 46 at a point adjacent the "500 PSI" and "REFILL" markings thereon. A second electrical contact in the form of an elongate strand of electrically conductive wire 76 extends generally centrally through the tube 72 and terminates in an inwardly looped or hooked free end 78 which protrudes through the opening 76.

In accordance with the present invention, and as shown in phantom in FIG. 6, the indicator 68 is adapted to be swept along the plate 46 into contact with the looped end 78 of the wire 76 in response to a drop in the pressure acting within the bourdon tube 56. As a result of the contact, the end 78 of the wire 76 is in turn swept into contact with the surface 76 of the tube 72 to complete or close an electrical alarm energization circuit and actuate a low pressure alarm in a manner as will be described later with reference to FIGS. 9–11. FIGS. 5 and 6 depict the embodiment of the present invention where the indicator 68 does not form part of the switch energization and activation circuit. It is understood, of course, that the invention encompasses embodiments where the indicator 68 forms part of the alarm energization circuit such as, for example, where the tube 72 is substituted with the indicator 68 and the circuit is completed as a result of contact between the indicator 68 and the wire 76.

FIGS. 7 and 8 depict alternate embodiments of the electrical switch 71 depicted in FIG. 6. The switch embodiment 171 depicted in FIG. 7 is similar in structure to the switch embodiment 71 of FIG. 6 except that the wire contact 176 depicted therein includes a free end 178 bent at approximately a 45 degree angle rather than a looped end as with the wire contact 76 shown in FIG. 6. The indicator 68 is adapted to contact the wire 176 at the base of the bent end 178 and then, as shown in phantom, sweep the end 178 into contact with the tube 172 as is shown in phantom in FIG. 7.

In the switch embodiment 271 of FIG. 8, the first contact is in the form of an elongate strand of electrically conductive wire 279 extending through the tube 272 and the second contact is in the form of a second elongate strand of electrically conductive wire 276 including a free hook shaped end 278. The indicator 68 is adapted to contact the wire 276 at the base of the hooked end 278 and then, as shown in phantom, sweep the end 278 into contact with the tip of the wire 279 to complete the switch circuit and actuate the alarm as described below in more detail.

The electrical components and alarm energization circuitry which allows for the activation of the low pressure alarm will now be described with reference to FIGS. 9–11.

Figure 11:
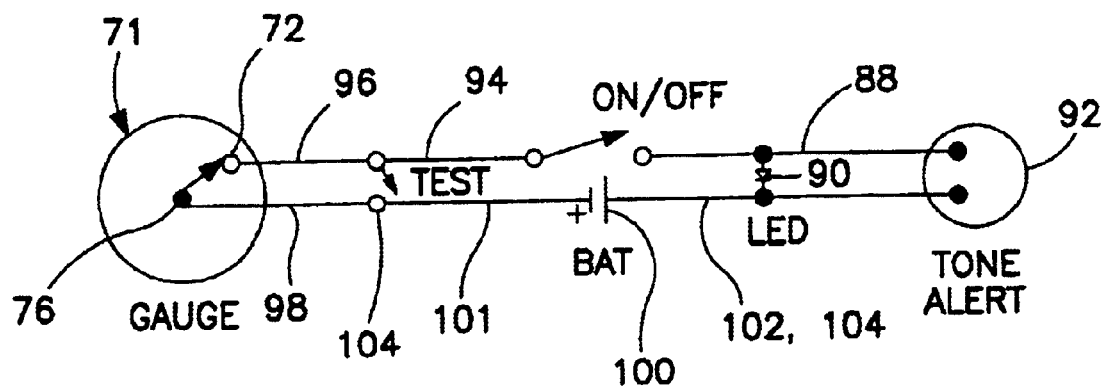
FIG. 11 is a schematic diagram of the alarm circuit of the assembly of the present invention.

FIGS. 9 and 10 depict the back face 80 of the housing 24 which houses an alarm circuit board 82 and associated energization circuit components which are shown schematically in FIG. 11. Particularly, the housing 24 incorporates an off/on switch 84 and associated switch box (not shown) which, via wire lead 86 and circuit board conductive strip segment 88, is electrically connected to a visual alarm component which, in the embodiment shown, comprises a light emitting diode (LED) 90 which is mounted to and extends outwardly from the top of the housing 24. The circuit board strip segment 88 also electrically conductively connects the off/on switch 84 to an audible alarm component which, in the embodiment shown, is an electric buzzer 92 which is mounted the back face 80 of the housing 24. The off/on switch 84 is also electrically connected to the circuit board conductive strip segment 94 and the wire lead 96 which, in turn, is electrically connected to the tube 72 of switch or gauge 71 (FIGS. 3, 4, and 6). FIG. 11 depicts the on/off gate in the open position.

A wire lead 98 (FIGS. 3, 4, and 6) electrically connects the contact wire 76 of the switch 71 to a battery 100 via battery wire lead 101 which in turn, via battery wire lead 102 and circuit board conductive strip segment 104, is electrically connected to both the LED 90 and the buzzer 92.

The housing 24 additionally incorporates an alarm test button 104 and an associated switch box (not shown) which is electrically connected to the off/on switch 84 via the circuit board conductive strip segment 94 and to the battery 100 via the battery wire lead 101. The test button 104 is also electrically connected to the switch 77 via wire leads 96 and 98. FIG. 11 shows the test gate in the open position.

In accordance with the present invention, the electrical circuit of the assembly 20 allows the alarm to be tested prior to installation to the manifold of an oxygen tank simply by turning the on/off switch 84 to the "on" position which closes the on/off gate and activates the buzzer 92 to sound and the LED 90 to flash as a result of the closed circuit created by the switch contact between the tube 72 and the wire 76.

Once the assembly 20 has been successfully tested prior to installation, the switch 84 can be turned to the "off" position and the assembly 20 can be installed to the manifold of an oxygen tank with the oxygen source off. Once the assembly has been installed, the on/off switch 84 of the assembly 20 can be turned to the "on" position and the alarm (i.e., the buzzer 92 and the LED 90) will be automatically activated as described above as a result of the contact between the indicator 68 and the wire 76 which causes contact between the tube 72 and the wire 76 to close the alarm circuit. The alarm will deactivate when the oxygen gas source is turned on and the pressure increases past approximately 500 PSI to cause the indicator 68 to be swept clockwise along the periphery of the face 46 away from the wire 76 thereby breaking the contact between the tube 72 and the wire 76 and opening the alarm circuit.

Moreover, in accordance with the present invention, the alarm can be tested while the assembly 20 is in use with the on/off switch 84 in the "on" position and the oxygen gas source turned on simply by depressing the test button 104 which, referring to FIG. 11, closes the test gate and completes the alarm circuit and causes the buzzer 92 to sound and the LED 90 to flash.

When the pressure of the fluid pressure source as measured by the assembly 20 decreases below to a level of approximately 500 PSI during use, the indicator 68 will sweep back counterclockwise along the face 46 into contact with the wire 76 which in turn, will cause the wire 76 to contact the tube 72 to close the normally open switch 71 and activate the audible and visual alarms as described above.

Figure 12:
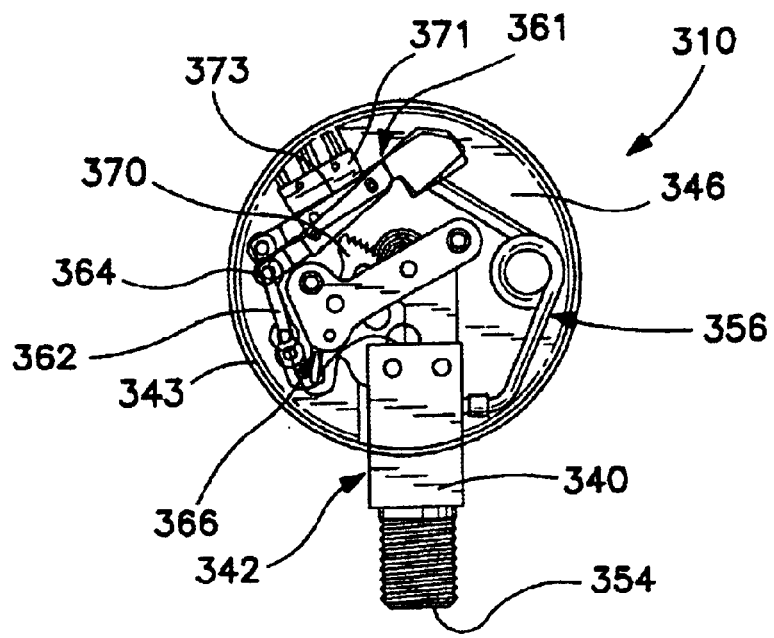
FIG. 12 is an elevational view of the interior structure of the housing of FIG. 3 including an alternate alarm switch embodiment incorporated therein.

An alternate embodiment of a low pressure alarm assembly 320 is depicted in FIG. 12. The assembly 320 of FIG. 12 differs in structure and operation from the assembly 20 of FIGS. 1–11 in that the indicator 68 is separate from the alarm energization circuit and the switch 71 of the assembly 20 has been substituted with a micro-switch or proximity switch 371 located in the housing 343 and the linkage on the back of the face 346 for measuring the fluid pressure includes an elongate gauge arm 361 which lies over the top elongate segment 159 (not shown) corresponding to the tube segment 59 shown in FIG. 9. The remaining elements of the associated linkage for measuring and indicating the fluid pressure are similar in structure and function to those described above in connection with the assembly 20 and have been designated by like reference numerals in the 300 series but having the same last two digits. The description of the assembly 20 above also applies to the assembly 320 unless described otherwise.

In accordance with this alternate embodiment, the proximity switch 371 is mounted to the back of the face 346 adjacent the flat top surface 373 of the arm 361 and a pivotable contact 375 on the switch 371 is adapted to be depressed by the arm 361 when the arm 361 is moved upwardly towards the switch 371 as shown in phantom in response to the movement of the bourdon tube 356. The depression of the contact 375 causes the switch 371 to shift from an open to a closed position which causes the activation of the audible and visual alarms using alarm circuitry similar to the circuitry described above with respect to the assembly 20.

It is understood, of course, that the two assembly embodiments shown in the FIGURES and described herein represent but two of the embodiments which fall within the scope of the invention and that numerous variations and modifications of the embodiments described alone may be effected without departing from the spirit and scope of the novel features of the present invention. It is to be understood that no limitation with respect to the specific embodiments illustrated herein is intended or should be inferred. It is, of course, intended to cover by the appended claims all such modifications as fall within the scope of the claims. For example, and although not shown, it is understood that the electrical switch and alarm components could be substituted with a whistle mountable within the housing 22 and operably associated with the bourdon tube 156 into a first pressure-biased closed, inoperative position at indicated pressures above 500 PSI and a second spring-biased open or whistling position when the pressure decreases below approximately 500 PSI. It is also understood that the proximity switch 371 could also be mounted to the front of the face 346 and that the actuator 68 could be adapted to be swept into contact with the proximity switch to complete the required alarm energization circuit.

We claim:

1. A low pressure alarm assembly comprising:

a first housing;

an inlet fitting in the first housing for connecting the alarm assembly to a source of fluid pressure;

a pressure responsive element in the first housing having one end in fluid communication with the source of fluid pressure and an opposite closed end movable in response to a change in fluid pressure in the fluid pressure source;

a linkage assembly operably coupling the pressure responsive element to a pressure indicator for indicating the pressure in response to the movement of the pressure responsive element;

an alarm energization switch in the first housing operably coupled to the linkage assembly and actuable in response to a predetermined movement of the linkage assembly for activating a low pressure alarm; and a second alarm housing separate from said first housing and containing an alarm circuit operably associated with the alarm energization switch in the first housing;

wherein the first housing includes a dial face with selected pressure markings and the indicator sweeps the face in response to the movement of the pressure responsive element, the alarm energization switch having first and second contacts extending outwardly through the face of the first housing and the indicator is adapted to abut and force the second contact into abutting relationship with the first contact for closing the alarm circuit and activating the alarm in response to the movement of the indicator to a predetermined low pressure marking.

2. The low pressure alarm assembly of claim 1 wherein the first contact is a tube extending through the first housing and defining an opening in the face, the second contact comprising an elongate wire extending through the tube and terminating in an end protruding through the opening defined in the tube, the indicator being adapted to abut and force the end of the second contact into abutting relationship with the tube for closing the circuit and activating the alarm.

3. A low pressure alarm assembly comprising:

a housing, an inlet fitting on the housing for connecting the alarm assembly to a source of fluid pressure;

a pressure tube in fluid communication with the source of fluid pressure and including a closed end movable in response to a change in the fluid pressure;

a lever assembly in the housing and operably associated with the pressure tube and actuable in response to the movement of the pressure tube;

a face including selected pressure markings thereon and an indicator operably associated with the lever assembly and adapted to be swept on the face in response to the actuation of the lever assembly; and an electrical switch including first and second contacts having respective ends protruding through the face, the indicator being adapted to contact and sweep the second contact into abutting relationship with the first contact for closing the switch and actuating a low pressure alarm.

4. The low pressure alarm assembly of claim 3 wherein the first contact is a tube extending through the housing and defining an opening in the face, the second contact comprising an elongate wire extending through the tube and terminating in an end protruding through the opening in the tube contact, the indicator being adapted to contact and sweep the end of the second contact into abutting relationship with the tube for closing the circuit and activating the alarm.

5. The low pressure alarm assembly of claim 3 wherein the alarm comprises a buzzer and an LED operably associated with the switch through a battery located in the housing.

6. The low pressure alarm assembly of claim 5 further comprising an actuable test switch operably electrically connected to the buzzer and the LED and the battery.

7. The low pressure alarm assembly of claim 6 further comprising an actuable switch marked on-off and operably electrically connected to the buzzer and the LED and the switch and the battery.

* * * * *